United States Patent [19]

Krüger

[11] 4,454,887
[45] Jun. 19, 1984

[54] MEDICAL INSTRUMENTS FOR INTRODUCTION INTO THE RESPIRATORY TRACT OF A PATIENT

[76] Inventor: Christian Krüger, Curtiusstrasse 4, 2400 Lübeck, Fed. Rep. of Germany

[21] Appl. No.: 367,408

[22] Filed: Apr. 12, 1982

[30] Foreign Application Priority Data

Apr. 15, 1981 [DE] Fed. Rep. of Germany ....... 3115192

[51] Int. Cl.³ .......................................... A61M 25/00
[52] U.S. Cl. ............................... 128/772; 128/207.14; 604/280; 604/45
[58] Field of Search ................... 128/716, 4, 747, 749, 128/750, 760, 768, 772, 200.18, 200.26, 7, 207.14, 8, 10, 207.15; 604/40, 43, 45, 96, 103, 167, 169, 256, 264, 280

[56] References Cited

U.S. PATENT DOCUMENTS

| | | | |
|---|---|---|---|
| 2,862,498 | 12/1958 | Weekes | 604/280 X |
| 3,799,173 | 3/1974 | Kamen | 604/96 X |
| 3,895,632 | 7/1975 | Plowiecki | 604/169 |
| 4,168,703 | 9/1979 | Kenigsberg | 604/45 X |
| 4,230,108 | 10/1980 | Young | 128/207.15 |
| 4,364,394 | 12/1982 | Wilkinson | 604/96 |

FOREIGN PATENT DOCUMENTS

| | | | |
|---|---|---|---|
| 3007994 | 9/1980 | Fed. Rep. of Germany | 128/4 |
| 2459051 | 2/1981 | France | 128/768 |
| 610529 | 5/1978 | U.S.S.R. | 128/768 |

Primary Examiner—C. Fred Rosenbaum
Assistant Examiner—Michelle Lester
Attorney, Agent, or Firm—Balogh, Osann, Kramer, Dvorak, Genova & Traub

[57] ABSTRACT

The invention relates to a medical instrument for withdrawal of tracheobronchial secretions or for introduction of curative agents, tubes, guiding elements, probes, endoscopes, catheters and the like into the respiratory tract of a patient.

A tube which is flexible and morphologically stable in cross-section, is inserted via the patient's mouth and pharynx cavities, and may be inserted with a distal extension as far as into the esophagus. Above the extension, the tube has an opening which is lined up laterally with the larynx cavity of the patient when the instrument is being inserted and through which the secretion is extracted. Also, the curative agents, guiding elements, tubes, probes, endoscopes, catheters and the like are inserted through this opening into the respiratory tract.

3 Claims, 17 Drawing Figures

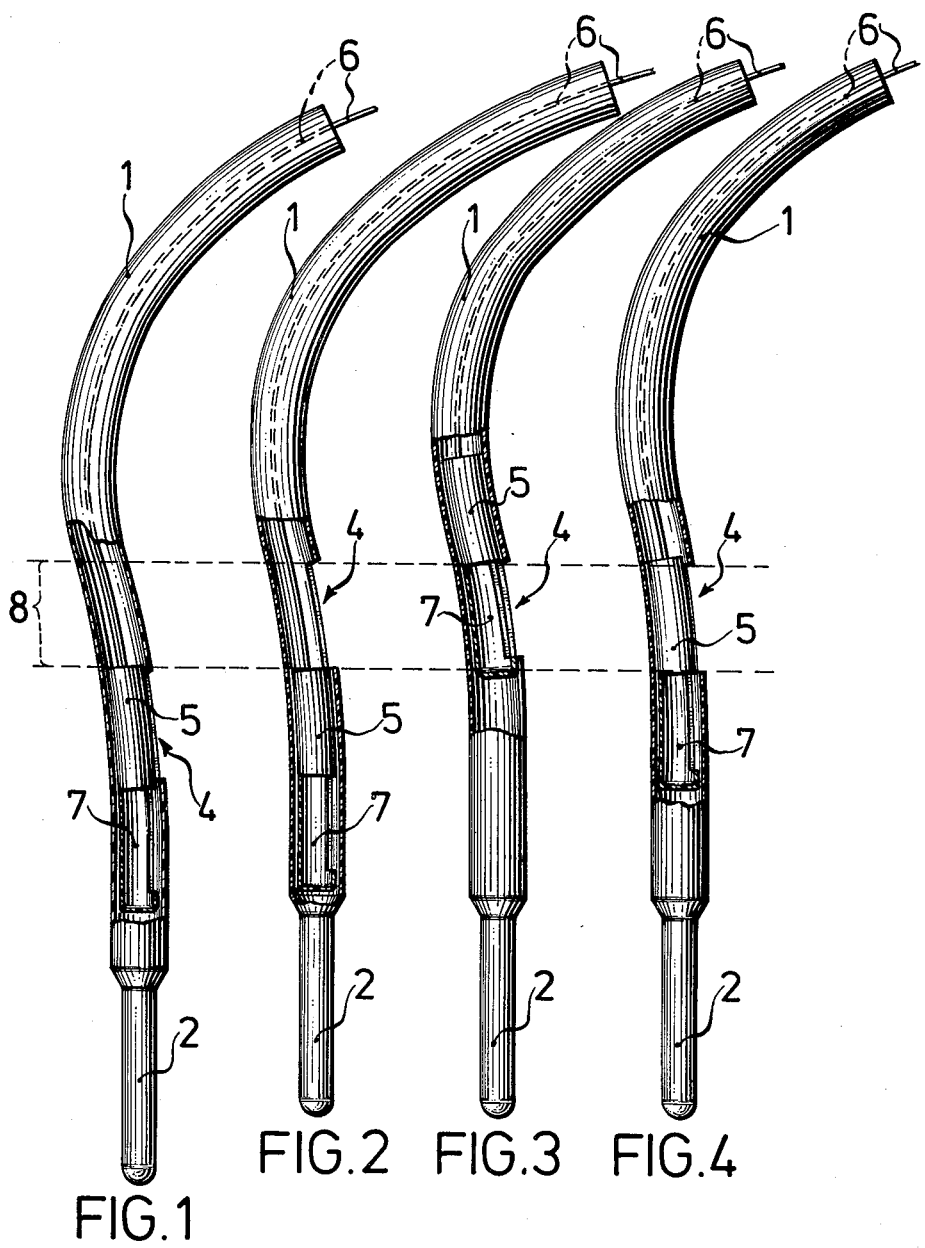

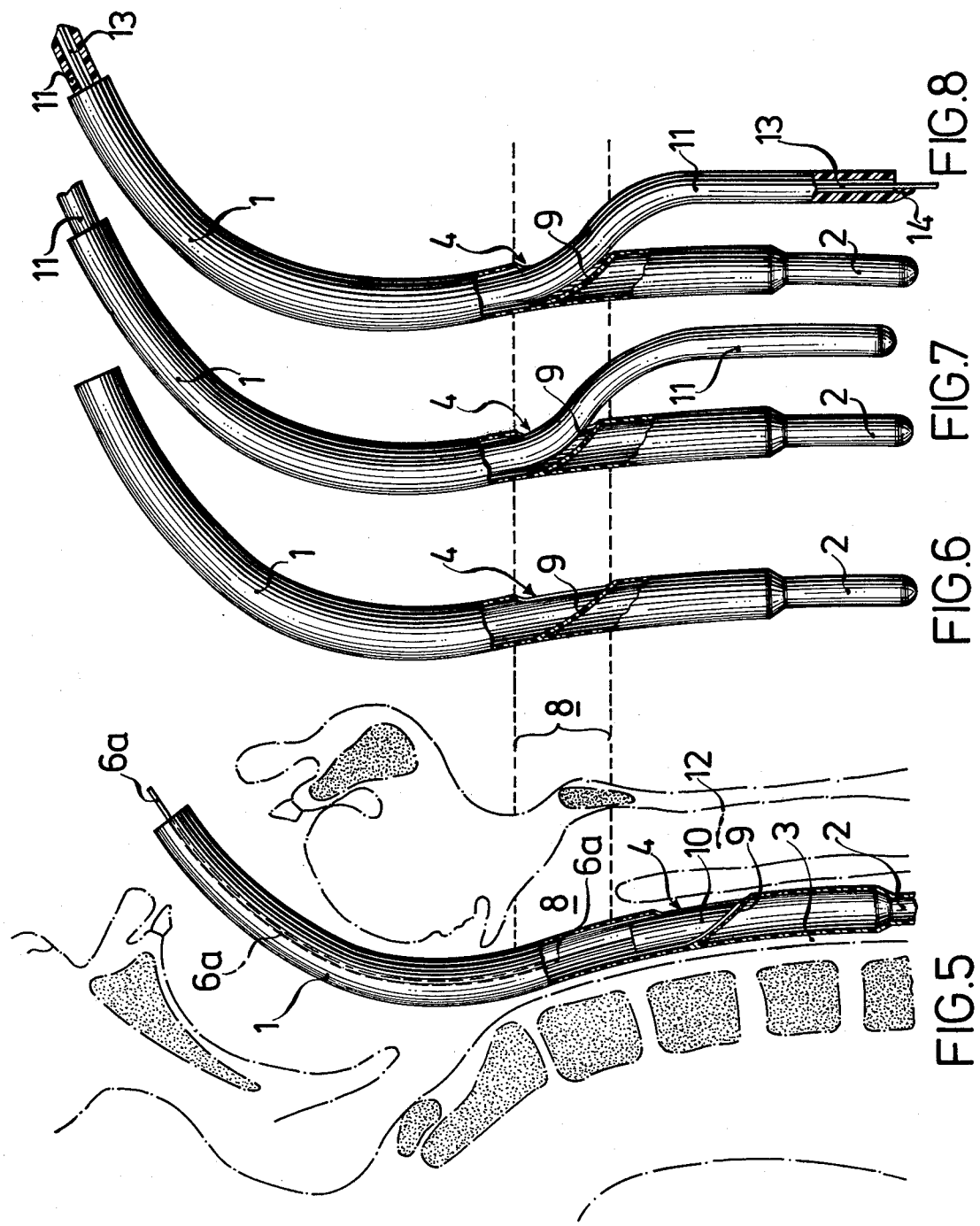

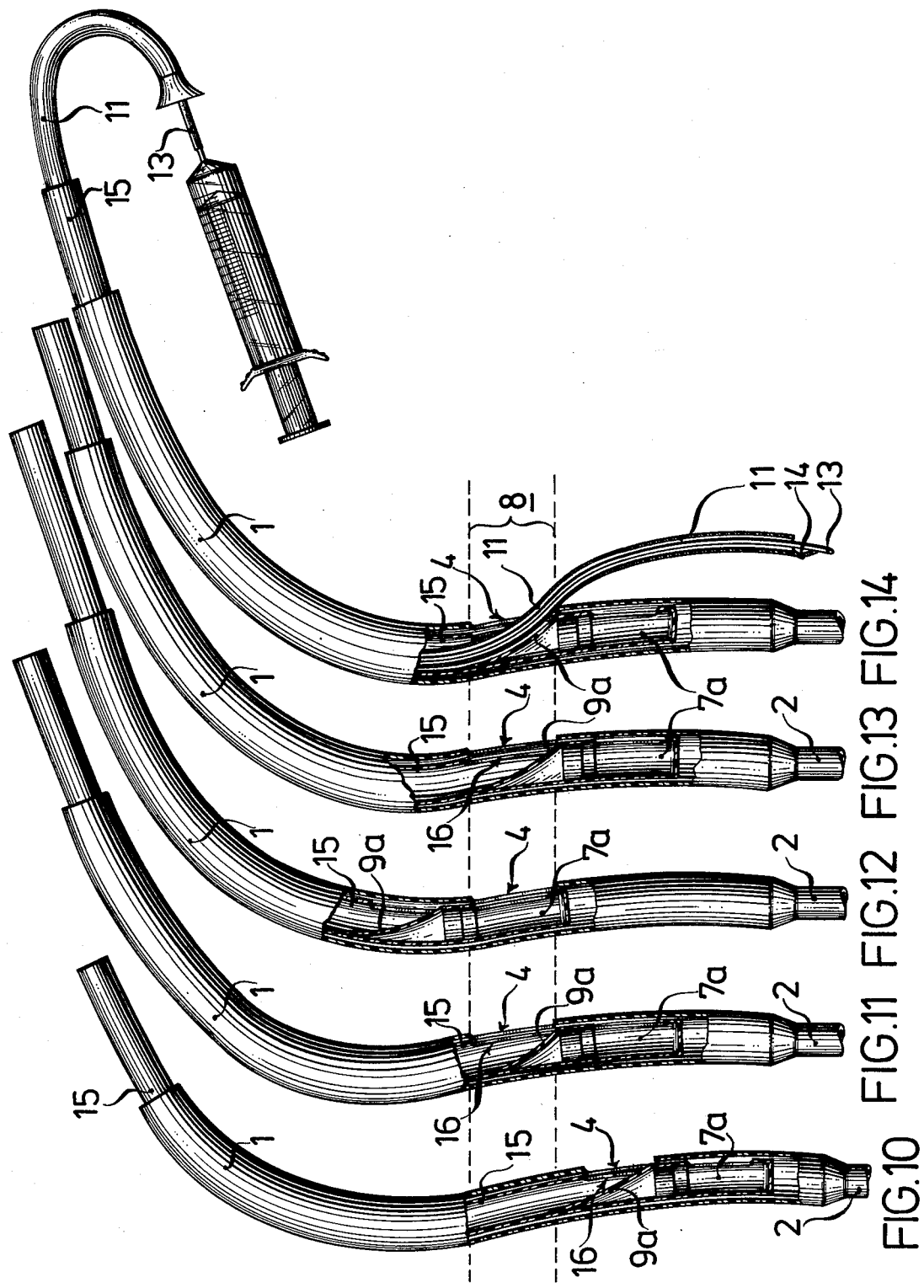

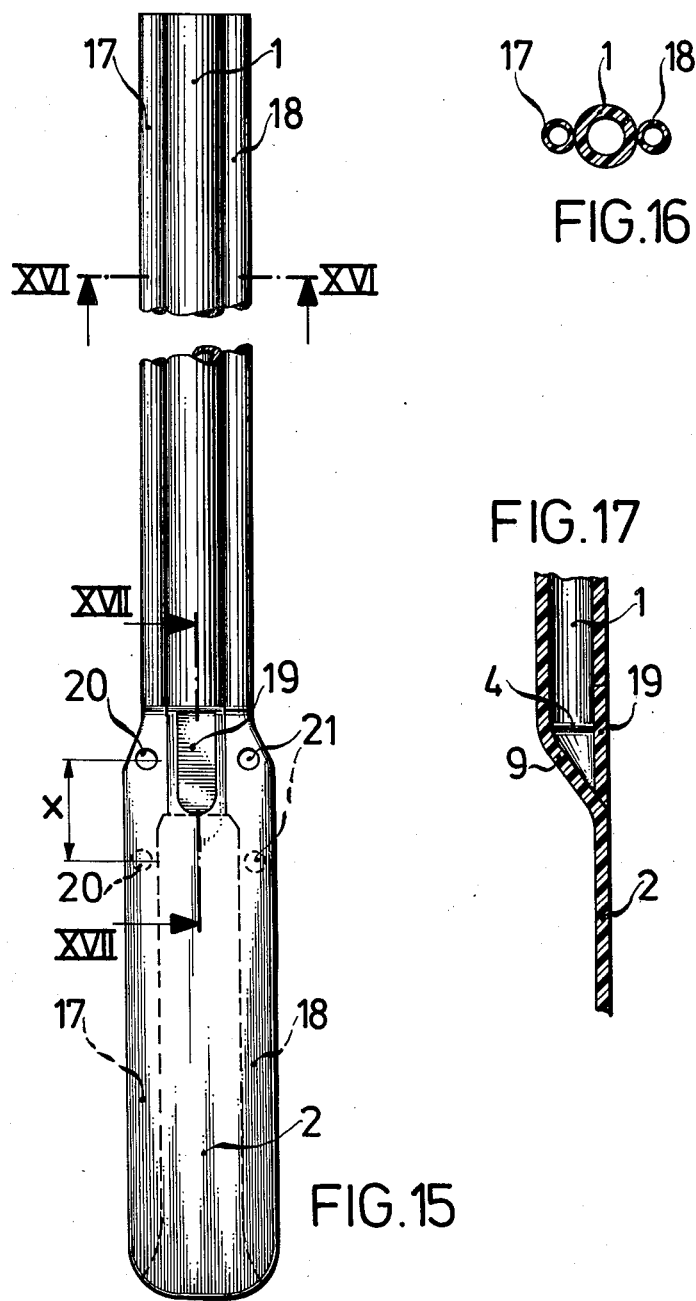

MEDICAL INSTRUMENTS FOR INTRODUCTION INTO THE RESPIRATORY TRACT OF A PATIENT

BACKGROUND OF THE INVENTION

The present invention relates to medical instruments for introduction into the respiratory tract of a patient e.g. for withdrawing tracheobronchial secretions or for the introduction of curative agents, tubes, guiding elements, probes, endoscopes, catheters and the like.

Upon diagnosing intrathorac complaints, it is possible to examine bacteriologically tracheobronchial secretions of a patient. If the secretion is sampled from the mouth and pharynx cavities, it is unavoidable to take a proportion of saliva as well, so that a separation of the tracheobronchial secretion from the saliva becomes necessary. This may normally be performed only by trained personnel in laboratories, at corresponding cost.

It may also be possible to draw off tracheobronchial secretions by means of bronchoscopes, or to perform a transtracheal aspiration. These two methods are, however, equally onerous and may be applied only be skilled practitioners. Finally, particular risks also arise for the patient under application of these methods.

Another problem also frequently arises in introducing curative agents or catheters, probes and the like into the patient's respiratory passages and in placing these at the target point at which, for example, an examination, a withdrawal of secretion or a treatment with curative agents, is necessary. These measures may be performed only by experienced practitioners with the known and conventional techniques.

It is an object of the invention to provide an instrument for these purposes which is inexpensive to manufacture, is relatively uncomplicated in its application and whereby it is possible to withdraw tracheobronchial secretions directly and without any proportion of saliva. It is a further object that the instrument be appropriately rendered trouble-free and be precisely directed to introduction of remedies, probes, catheters and the like into the respiratory tract.

SUMMARY OF THE INVENTION

To achieve the aforementioned and other objects, the invention provides for a medical instrument for insertion into the respiratory tract of a patient, including a flexible tube insertable through the mouth and pharynx cavities of the patient (the tube is morphologically stable in cross-section) up to and into the esophagus by means of a distal extension. The tube has an opening located above the extension, which on insertion of the instrument, is laterally alignable with the larynx of a patient. Accordingly, secretions may be extracted from the respiratory tract, or curative agents, tubes, guiding elements, probes, endoscopes, catheters and the like may be inserted into the respiratory tract via the aforementioned opening.

A collector vessel or a culture medium carrier for bacteria may be displaced axially within the tube by means of an actuating element, to place an inlet opening of the collector vessel in coincidence with the tube opening, (the collector vessel being combined with a shutter which covers the tube opening as soon as the collector vessel has been displaced in distal direction beyond the tube opening.) When the opening of the collector vessel and the opening of the tube are congruent and both openings are aligned with the larynx cavity, the patient may be induced to cough so as to bring tracheobronchial secretions into the collector vessel. Following this, the collector vessel may be drawn out of the tube and the secretion present in the collector vessel may be examined.

The instrument may further be provided with a sloping baffle or partition which extends in the area of the tube opening (extending from the rearward wall surface of the tube with a forwardly and downwardly directed inclination from the above) and establishes an even transition to the bottom distal portion of the tube opening, so that a catheter, an internal tube, a guiding element, a probe, a flexible endoscope or the like, which is inserted into the tube at the proximal side, may be pushed into the trachea along the baffle. In this manner, a curving agent may be directed at the precise target point at which a treatment is required, e.g. via a catheter introduced into the trachea or via a correspondingly inserted probe. On the other hand, secretion may be drawn off by suction at an optional point within the respiratory tract by means of the catheter or probe.

BRIEF DESCRIPTION OF THE DRAWINGS

In order that the invention may be more clearly understood, reference will now be made to the accompanying drawings which illustrate certain embodiments thereof by way of example and in which:

FIGS. 1 to 4 show a first embodiment in longitudinal cross-section,

FIGS. 5 to 8 show a second embodiment in longitudinal cross-section,

FIGS. 9 to 14 show a third embodiment in longitudinal cross-section,

FIG. 15 shows a front view of a fourth embodiment,

FIG. 16 shows the cross-section XVI—XVI through the instrument according to FIG. 15, and FIG. 17 shows a partial longitudinal cross-section XVII—XVII through the instrument according to FIG. 15.

DETAILED DESCRIPTION OF PREFERRED EMBODIMENTS

Figure 9:
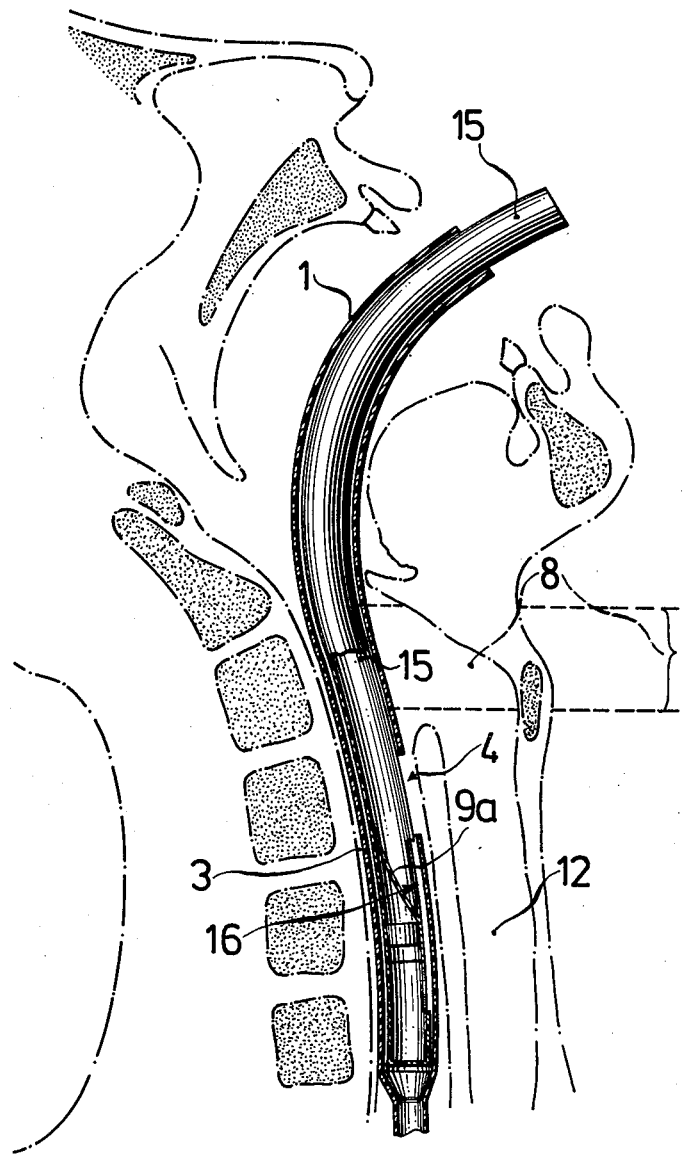

Referring now to the drawings, the instrument illustrated in FIGS. 1 to 4 includes a tube 1 insertable through the mouth and pharynx cavities of a patient, which is flexible but morphologically stable in cross-section and which is continued at its distal end by an extension 2, (if desired reduced to a smaller diameter). This extension may for example be a hose of a length of approximately 10 cms and which is closed at the end, and is formed of soft highly pliable material such as soft rubber or soft plastics material. The distal extremity of the tube including the extension 2 is inserted into the esophagus by appropriate swallowing motions by the patient, as illustrated in FIGS. 5 and 9 in connection with other embodiments. As for the rest, the tube 1 should be appropriately curved to correspond to the anatomical contours of the mouth and pharynx cavities.

The tube 1, (of a length of approximately 25 cms. for example), is provided with an oval opening 4, the major axis of which extends parallel to the longitudinal axis of the tube 1, at a distance of approximately 5 cms. from its distal end. This opening 4 may be closed off by means of a shutter 5 matching the internal diameter of the tube 1, which is displaceable within the tube by means of a wire 6. The shutter 5 is followed at the distal side by a culture medium plate or by a detachable collector vessel 7 with or without a culture medium for bacteria, which is open towards the opening 4. With the opening 4 closed, the tube 1 has a distal portion and the extension 2 being inserted into the esophagus 3 (FIG. 1), whereupon the shutter 5 with the collector vessel 7 are displaced in distal direction within the tube 1 and the tube 1 is then pulled out until the opening 4 is aligned with the larynx cavity 8 of the patient (FIG. 2). The doctor performing the treatment may determine this easily by inducing the patient to exhale with the mouth closed, so that breathing air can enter the tube 1 only through the opening 4 and will flow out at the proximal side, which may be detected by sound.

Since the length of the shutter 5 as well as the length of the open side of the collector vessel 7 are known, these two elements 5, 7 may thereupon be displaced in proximal direction within the tube 1 by a definite distance, until the inlet of the opening of the collector vessel 7 coincides with the opening 4 (FIG. 3). The patient may then be induced to cough or breathe out violently, to allow tracheobronchial secretions to reach the collector vessel 7. The opening is then closed again, as will be seen from FIG. 4, so that the tube 1 together with the shutter 5 and the collector vessel 7 may finally be extracted from the patient as a whole. The secretion present in the collector vessel is thus available for bacteriological or cytological examination. What is of importance is that saliva cannot penetrate into the collector vessel either during the insertion or during the withdrawal of the instrument, so that only tracheobronchial secretions are actually made available, (without other components), in the case of the steps described.

In the embodiment shown in FIGS. 5 to 8, use is also made of a tube 1 of the kind described above, with an extension 2 and an opening 4. This tube 1 is however provided in the area of the elongated oval opening 4 with a baffle 9 which runs slopingly downwards and forwards from above, from the rearward tube surface, and merges evenly into the distal end of the opening 4, (as most clearly apparent from FIG. 6). The baffle 9 may, for example, be produced in uncomplicated manner by cutting a flap out of the rearward tube wall, which is then bent over towards the front to correspond to the shape of the baffle 9 and rests on the distal periphery of the opening 4.

A shutter 10 for closing of the opening 4 is also inserted into the tube 1 by means of a wire 6a, in this case. The distal end of this shutter is matched to the outline of the baffle 9 (FIG. 5). The tube 1 so prepared, with the opening 4 closed, is again inserted with its distal end and extension 2 into the esophagus 3 via the mouth and pharynx cavities, that is to say in such manner that the opening 4 is distally situated with respect to the larynx cavity 8 (FIG. 5). After the shutter 10 has been withdrawn from the tube 1, the tube 1 is drawn back until the tube opening 4 is in alignment with the larynx cavity 8 (FIG. 6). The physician will easily be able to detect this position by inducing the patient to breathe out. A tubular probe 11 which is deflected sideways by the baffle 9 and finally enters the trachea 12 (FIG. 7) is then pushed into the tube 1 from the proximal extremity.

A flexible catheter 13 (FIG. 8) which may be advanced into the bronchial passages so that tracheobronchial secretions may be drawn off via the catheter 13 from the region of the bronchial passages, may be led through this probe 11. On the other hand, a curative agent may also be introduced into the respiratory tract via the catheter 13. The probe 11 is appropriately provided at its distal end with an easily opened seal which may be opened by the catheter pushed through. For example, this shutter or seal comprises an elastic tongue or lip 14 (FIG. 8) projecting beyond the distal end of the probe 11 and covering said extremity, which may be recurved into the distal end of the probe and which may be extruded out of the probe end again by the distal end of the catheter 13 which is to be pushed through. Upon inserting the probe into the trachea, this seal 14 prevents penetration of saliva into the probe or into the catheter 13.

The tube 1 is also constructed as described in the foregoing, in the embodiment illustrated in FIGS. 9 to 14. In this case however, the tube opening 4 is shut off during insertion of the instrument by the periphery of an internal tube 15 which is to be inserted into the tube 1. The tube 15 has an opening 16 which may be placed in coincidence with the opening 4.

Upon inserting the instrument, the internal tube 15 shuts off the opening 4 of the tube 1 with its peripheral side situated proximally from the opening 16, as apparent from FIG. 9. The two openings 4 and 16 are then placed in coincidence in accordance with the dimensions selected, by displacing the internal tube 15 within the tube 1. A baffle 9a which is situated in the area of the opening 16 (FIG. 10) is situated in the internal tube 15. The external tube 1 and the internal tube 15 are then displaced in proximal direction until the two openings 4 and 16 have been placed in coincidence with the larynx cavity 8 (FIG. 11). The physician may again easily check whether this position has been reached, by causing the patient to exhale.

A culture medium carrier or a collector vessel 7a which is releasably connected to the probe 15 at the distal side, (for example by means of an adaptor), is positioned with the open side or inlet facing towards the larynx cavity 8, so that secretions may then again be placed in the collector vessel 7a or on the culture medium from the respiratory tract in the manner hereinabove described. Notwithstanding whether the collector vessel 7a is included or omitted from the action, it is also possible to proceed on the basis of the baffle position 9a shown in FIGS. 11 and 13, in such manner as described hereinafter. A tabular probe 11 containing a catheter 13 (FIG. 14) is pushed through the internal tube 15, the catheter again being deflected sideways by the baffle 9a passing through the opening 4 and entering the trachea 12, the catheter 13 being feedable forward as far into the bronchial passages so as to draw secretions from the bronchial passages via the catheter, or to introduce curative agents into the area of the bronchial passages.

FIGS. 15 to 17 finally show an instrument wherein two breathing or venting tubes 17, 18 joined to the tube 1 extend parallel to the tube 1. The tubes 17, 18 are open at the proximal side and each has a distal opening 20, 21 close to the opening 4 of the tube 1, covered by the tongue 19. The three tubes 1, 17 and 18 are advantageously made in one piece or formed integrally by extrusion from plastics material. The section produced in this manner is then cut to appropriate length. The extremity of the section forming the extension 2 is then pressed flat under application of heat, so that a substantially plane strip is formed. The extension 2 may however also be formed with a bend or slight curvature as seen in cross-section, in order to secure thereby an adaptation to the anatomically predicated cross-sectional shape of the esophagus. The tongue 19 is formed by cutting through the tube 1 in accordance with the outline of the tongue. The two holes 20 and 21 are produced by punching material out of the two tubes 17 and 18.

In contrast to the form or shape illustrated in FIG. 15, the two venting tubes 17, 18 may also merge into the entension 2 beyond their distal openings 20, 21 and form its longitudinal sides as shown dotted in FIG. 15. This offers the advantage that the patient may swallow the distal extremity of the instrument more easily, without the risk of acute edges of the extension 2 being troublesome whilst doing so.

As for the rest, the patient will also ingest the instrument so far by swallowing motions, so that the tongue 19 covering the opening 4 and the openings 20, 21 are situated within the esophagus 3. The physician will thereupon pull the instrument in proximal direction. As soon as the opening 20, 21 come into coincidence with the larynx cavity 8, the patient can blow air breathed into the tubes 17, 18 through these openings, by exhaling. The physician detects this by sound. He is then aware that the opening 4 of the tube 1 is at least approximately situated in the correct position. By complementary withdrawal of the instrument through a definite distance x, the opening 4 may finally be aligned precisely and centrally with the larynx cavity.

If it is desired however to make assurance doubly sure, to ascertain that the opening of the tube 1 covered by the tongue 19 is placed in the absolutely correct position for the remedial action, the openings 20, 21 could also be arranged staggered a little farther towards the distal side by the distance x as shown dotted in FIG. 15. As soon as it is then possible (upon withdrawing of the instrument) to establish that the patient can already breathe air into the tubes 17, 18 via the openings 20, 21, the physician need not pull the instrument out any farther. As for the rest, it is evident that the distance x should be dimensioned in accordance with the anatomical conditions.

As also described in the foregoing in connection with the other embodiments, other tubes, probes or catheters may be inserted into the tube 1. These slide along the baffle 9 and flexibly deflect the tongue 19, so that the opening 4 is freed for continued insertion of the elements in question into the trachea.

Among others, the special advantages of this instrument should be considered to include the baffle 9 being formed in uncomplicated manner by appropriate shaping of the tube 1. Moreover, there is no need to shut off the opening of the tube 1, (which tube is to be inserted), by means of a special closure. Probes and catheters may even be inserted into the tube 1 during its introduction, since the verification of the correct position of the opening 4 may be performed during exhalation by the patient via the lateral tubes 17 and 18.

The instrument in accordance with the four embodiments described above is relatively uncomplicated as regards manufacture as well as application. As already stated, secretions may safely be extracted with an instrument of this nature. Furthermore, curative agents may be brought into application precisely at any target point within the respiratory tract. Furthermore, the instrument also offers some complementary possibilities of application, which are to be touched upon briefly in the following:

For example, the instrument shown in FIG. 6 may be utilized for insertion of other instruments, flexible endoscopes or breathing tubes, into the trachea. In doing so, (after insertion of a breathing tube), the instrument acting merely as an intubation means may be withdrawn leaving the breathing tube in the inserted position. The same procedure may be followed in the case of inserted endoscopes, remanent catheters, probes and the like, which should obviously also have a diameter of such dimension in the proximal region so that they can pass through the tube 1.

If, in these special cases of application, it is intended to keep the tube bore small, the tube 1 such as shown for example in FIG. 6 may initially merely have inserted through it and into the trachea a flexible wire intended to act as a guiding element, and the instrument may then be withdrawn while the wire remains in the inserted position. A breathing tube may then be threaded over this wire at the proximal side, and may be displaced into the trachea whilst being guided by the wire traversing it. Finally, the guiding wire is pulled out of the breathing tube remaining in the trachea.

Since these steps are commonly performed with patients under anaesthesia, and the patient cannot consequently perform any conscious swallowing motions, the flexible extension 2 may be omitted if appropriate, and the tube 1 may be formed a little longer than illustrated. As for the rest, the distal terminal portion of the tube 1 below the opening 4 should extend rectilinearly.

What is claimed is:

1. A medical instrument for insertion into the respiratory tract of a patient, comprising:
 a flexible tube which is morphologically stable in cross-section, and having a distal extension formed of a flat strip,
 said flexible tube being insertable by means of said extension through the mouth and pharynx cavities of the patient up to and into the oesophagus thereof,
 said flexible tube having an opening closable by means of a tongue located on said flexible tube, said opening of said flexible tube being located above said extension and, on insertion of the instrument, said opening is laterally alignable with the larynx of the patient, whereby secretions may be extracted from, and curative agents, internal tubes, guiding elements, probes, endoscopes and catheters are insertable into the respiratory tract of the patient via said flexible tube opening,
 partition, extending in the area of said flexible tube opening from the rearward wall area of said flexible tube slopingly downwards towards the front thereof, and establishing an even transition to the lower distal terminal portion of said flexible tube opening, so that a catheter, an internal tube, a guiding element, and an endoscope, which are insertable as the proximal extremity into said flexible tube, can be inserted into the patient's respiratory tract along said baffle or partition, and two air or venting tubes, which are open at the proximal side thereof, joined to said flexible tube and extending parallel thereto, each of said two air or venting tubes having a distal opening adjacent to said opening of said flexible tube, said extension having a width that is substantially equal to the width of the structure comprising the flexible tube and the two air or venting tubes.

2. An instrument according to claim 1, wherein said extension is made from soft and pliable material selected from the group of soft rubber and soft plastics material.

3. An instrument according to claim 1, wherein said air or venting tubes merge into said extension beyond their distal openings and form its longitudinal sides.

* * * * *